United States Patent [19]

Sterrett

[11] Patent Number: 5,171,225

[45] Date of Patent: Dec. 15, 1992

[54] PRESSURE ANESTHESIA DEVICE FOR GUIDING NEEDLES

[75] Inventor: John D. Sterrett, Halifax, Canada

[73] Assignee: Dalhousie College and University, Halifax, Canada

[21] Appl. No.: 647,974

[22] Filed: Jan. 30, 1991

[30] Foreign Application Priority Data

Feb. 2, 1990 [CA] Canada .................................. 2009245

[51] Int. Cl.[5] .............................................. A61M 5/00
[52] U.S. Cl. .................................... 604/112; 606/185; 604/116
[58] Field of Search ............... 606/201, 185, 189, 148; 604/112, 116; 433/102, 141, 75, 31

[56] References Cited

U.S. PATENT DOCUMENTS

| Re. 13,621 | 9/1913 | Kelly | 433/142 |
|---|---|---|---|
| 2,044,410 | 6/1936 | Thornberry | 128/215 |
| 2,479,645 | 8/1949 | Silverstein | 128/215 |
| 2,674,246 | 4/1954 | Bower | 128/215 |
| 4,681,101 | 7/1987 | Bicoll | 128/303 R |
| 4,784,139 | 11/1988 | Demos | 606/148 |
| 4,803,984 | 2/1989 | Narayanan et al. | 606/148 |
| 5,053,043 | 10/1991 | Gottesman et al. | 606/148 |

Primary Examiner—C. Fred Rosenbaum
Assistant Examiner—William W. Lewis
Attorney, Agent, or Firm—R. Craig Armstrong

[57] ABSTRACT

A pressure dental anesthesia device comprising a needle guiding element attached to a handle and having a tip suitable for pressing against a living tissue area to be anesthetized. The needle guiding element has an elongated cavity which narrows at the pressure tip to localize the needle and widens towards the distal end of the cavity so as to facilitate the positioning and guidance of the hypodermic needle in the cavity at a safe distance from the tissue.

6 Claims, 1 Drawing Sheet

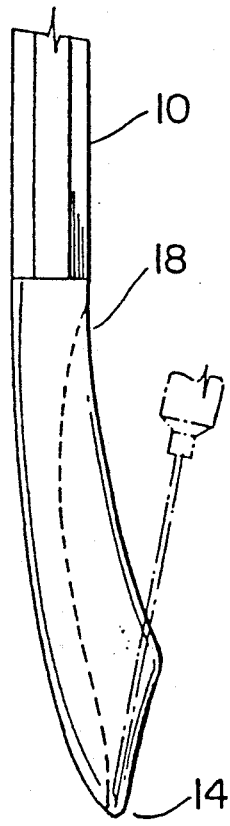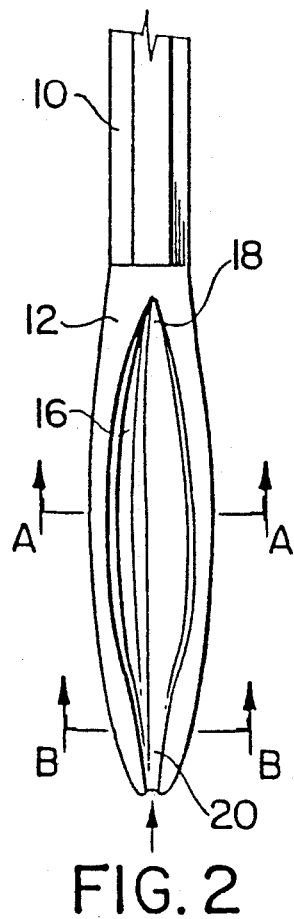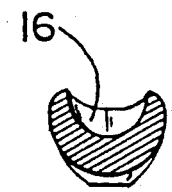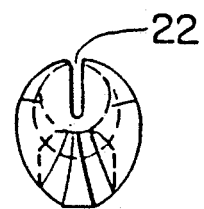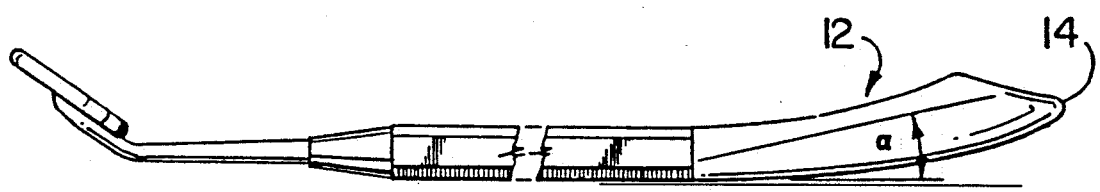
FIG. 1
FIG. 2
FIG. 3
FIG. 4
FIG. 5
FIG. 6

PRESSURE ANESTHESIA DEVICE FOR GUIDING NEEDLES

BACKGROUND OF THE INVENTION

1. Field of the Invention

This invention relates to a device for temporarily anesthetizing a living tissue by applying a pressure on the tissue, particularly in order to alleviate or reduce the sensation of pain associated with the subsequent puncturing of living tissue. In particular, it relates to a pressure anesthesia device useful in dental procedures.

2. Description of the Prior Art

It is well known that certain areas of the human body are more sensitive to pain than others. This is particularly true for the tissues of the oral cavity. Therefore, it is often necessary to anesthetize oral tissues prior to the initiation of dental procedures. To reduce the pain associated with the dental procedures, an anesthetic can be injected into the gum or palate by means of an injection needle. However, the injection itself, and particularly the puncture of the living gum or palate tissue is quite painful. It has therefore been desirable to reduce the pain associated with the insertion of an injection needle.

This goal can be attained by local cooling. Another approach, more often used and taught, is pressure anesthesia which is based on a long-known phenomenon of the puncture pain being partially masked by a lesser pain sensation influenced by pressing a solid object against the body area to be punctured. This phenomenon is particularly occuring in the oral areas.

A number of devices utilizing this pressure anesthesia effect have been proposed to date. For instance, U.S. Pat. No. 2,479,645 to Silverstein describes an instrument with an approximately spherical bead to be pressed against the tissue. The bead has a straight diametrical opening for a hypodermic needle to be passed there through, and a bottomless slot extending over the length of the opening to the part of the bead which comes into contact with the tissue to be punctured. The slot has a width less than the diameter of the opening. This enables the device to be withdrawn from the patient's mouth while the needle is still inserted.

U.S Pat. No. 4,681,101, issued Jul. 21, 1987, to Bicoll discloses a device with one or two disc-shaped bodies having each an aperture there through. The flat body is placed and pressed against the surface of the living tissue to anesthetize it and then an injection needle is passed through the aperture into the tissue.

The above mentioned devices do not address the problem of locating the opening or aperture in the pressure tip of the device with the hypodermic needle. The problem is easily appreciated when considering that, for example, the diameter of the Bicoll aperture is 1 mm. The task of inserting the needle into a small opening in the spherical bead of Silverstein appears to be quite difficult as well.

U.S. Pat. No. 2,044,410 issued Jun. 16, 1936 to Thornberry attempts to solve the problem. In the device disclosed therein, an upturned tongue at the end of a dental instrument, in the vicinity of a passage, serves to guide the needle toward the passage and to protect the tissue from inadvertent sticking.

Although the Thornberry device is useful, it has certain limitations in that it does not eliminate the possibility of unwanted sticking and is relatively bulky. In addition, it does not have a slot for the safe withdrawal of the device once the needle is inserted. Accordingly, there still is a need for a relatively safe and effective instrument for carrying out dental pressure anesthesia.

SUMMARY OF THE INVENTION

According to the invention, there is provided a device for carrying out pressure anesthesia before a hypodermic injection, the device comprising a handle, a hypodermic needle guiding element attached to the handle at one end and having a pressure tip at the distal end, the pressure tip adapted to be pressed against a tissue to be anesthetized.

The needle guiding element comprises a slide one end of which is spaced from the pressure tip by a safety distance and the other end of which is adjacent the pressure tip, the width of the slide at least at said one end being such as to enable an operator to easily locate the slide manually with a hypodermic needle when the device is located in a patient's mouth.

Preferably, the slide is narrowed in the vicinity of the pressure tip so as to limit a lateral movement of the hypodermic needle while allowing for its passage along the slide.

Preferably, the device is associated with another dental instrument, e.g., a mirror or an explorer, by the common handle.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which:

FIG. 1 is a side view of the pressure anesthesia device showing a hypodermic needle in the position prior to injection;

FIG. 2 is a front view of the device of FIG. 1;

FIG. 3 is a view of the device of FIG. 2 from a direction indicated by the arrow in FIG. 2;

FIG. 4 is a cross-sectional view along the line A—A of FIG. 2;

FIG. 5 is a cross-sectional view along the line B—B of FIG. 2; and

FIG. 6 is a side view of a combined dental instrument comprising the device of the invention.

DETAILED DESCRIPTION OF THE PREFERRED EMBODIMENT

In the drawings and particularly in FIG. 1, a dental pressure anesthesia device is illustrated by way of a preferred embodiment. The device has a handle 10 with which is associated integrally a concave element 12 which at the distal end has a rounded pressure tip 14. In this embodiment, the tip does not constitute a conspicuous element but it is also conceivable to form the tip as a bead, with an approximately spherical shape. The element 12 has an elongated cavity 16 which extends from one end 18, proximate to the handle, to the distal end 20, adjacent the tip 14. In the vicinity of the tip 14, the cavity narrows to form a channel 22 which extends up to the pressure tip 14.

As illustrated in FIG. 3, the channel 22 has a U-shape, the arms of the U-shape distanced from each other so as to allow for a relatively easy passage of a hypodermic needle therebetween, along the channel 22 and for the withdrawal of the needle through the open end of the U-shape. However, the distance is such as to restrict a lateral movement of the needle, particularly at the tip 14, to a reasonable minimum; for example, a 0.5 mm clearance can be considered quite suitable for the above-described purpose.

As shown in FIG. 2, the cavity 16 has one end 18 spaced from the tip 14 by a safety distance. The term "safety distance" in this disclosure, means such a distance from an object at which it is practically safe to operate a hypodermic needle without an appreciable risk of inadvertently sticking the object (a living tissue) with the needle.

In particular, when the device is inserted into the mouth of the patient and the pressure tip is contacted with the predetermined spot in the oral cavity, it is desirable to find the bottom of the cavity 16 with the needle tip at a safe distance (i.e. the "safety distance") between the needle tip and the living tissue. This is achieved, according to the invention, when the first end 18 (upper end in FIG. 2) of the cavity 16 is distanced from the pressure tip 14 by at least about 30 mm. In the embodiment illustrated, that distance is about 40 mm.

It will be understood that the width of the cavity 16 is of great importance. It should be such that an average operator, typically a dentist, finds it relatively easy to place the tip of the hypodermic needle in the cavity so that the tip rests against the back wall of the cavity. This is accomplished when the width of the cavity exceeds 3 mm, and is preferably at least about 5 mm at least in the region of the cavity spaced from the pressure tip by the above-discussed "safety distance". Of course, the cavity may be relatively wide along most of its length, as shown in FIG. 2.

For manufacturing reasons, it may be difficult to make the cavity wide at the very end 18. It will be understood that the safety distance applies to the region of the cavity where it assumes the above-defined width.

As illustrated in FIGS. 4 and 5, when the needle of a hypodermic syringe is placed against the back wall of the cavity 16, it can be easily guided along the cavity towards the tip. In the region of the cavity represented by FIG. 4, it is relatively easy to move the needle tip laterally without leaving the cavity. As it extends toward the pressure tip (FIG. 5), the cavity smoothly becomes a narrow channel 22 where the lateral movement of the needle tip becomes much more restricted. In the direct vicinity of the tip, as shown in FIG. 3, the highest restriction is encountered. This allows for a very precise positioning of the needle tip at the anesthetized area.

It will be easily appreciated by those familiar with the field of dentistry that such a device can not be too bulky at the risk of obstructing the user's view. Therefore, the diameter of the concave element 12, should not exceed about 11 to 12 mm. This of course also limits the maximum width of the cavity 16. Consequently, the concave element 12, has an elongated shape, with its general longitudinal axis preferably inclined relative to the handle 10 by an angle $\alpha$ of about 5°–20° in order to facilitate an easy reach of every desired location in the oral cavity.

It is preferable that the device of the invention be located on an unused end of another dental instrument, e.g. a mirror or an explorer, these two instruments thus having a common handle.

In operation, the device is inserted into a patient's mouth, the pressure tip is placed against an area to be anesthetized and pressed thereagainst so as to achieve the anesthetizing effect. The hypodermic syringe is then aimed so that the needle tip is placed in the cavity 16, away from the pressure tip. The needle tip is then guided along the cavity and through the channel until it reaches the living tissue at the pressure tip 14 of the device. The injection is now effected and while the needle is inserted in the living tissue, the device can safely be withdrawn thanks to the channel 22 being open on one side. This, advantageously, frees the operator's one hand. When the injection is finished, the syringe is also withdrawn to complete the procedure.

It will be appreciated that the above description relates to the preferred embodiment by way of example only. Many variations on the invention will be obvious to those knowledgeable in the field, and such obvious variations are within the scope of the invention as described and claimed, whether or not expressly described.

What is claimed as the invention is:

1. A pressure anesthesia device comprising a handle, a hypodermic needle guiding element attached to the handle at one end and having a pressure tip at the distal end, the pressure tip being adapted to be pressed against a tissue to be anesthetized, the needle guiding element comprising a slide one end of which is spaced from the pressure tip by a safety distance and the other end of which is adjacent the pressure tip and is narrowed so as to limit lateral movement of the hypodermic needle while allowing for its passage along the slide, the width of the slide at least at said one end being such as to enable an operator to easily locate the slide manually with a hypodermic needle when the device is located in a patient's mouth.

2. The device according to claim 1, wherein the slide width is at least about 5 mm.

3. The device according to claim 1, wherein the "safety distance" is at least about 30 mm.

4. The device according to claim 1, wherein the needle guiding element is elongated in shape.

5. The device according to claim 1, wherein the needle guiding element extends at an angle from about 5° to about 20° relative to the handle.

6. The device according to claim 1, wherein the device is associated with another dental instrument by means of a common handle.

* * * * *